United States Patent
Pasin et al.

(10) Patent No.: US 11,708,500 B2
(45) Date of Patent: Jul. 25, 2023

(54) SOLVENT COMPOUNDS FOR USE AS COALESCENTS

(71) Applicant: TBF ENVIRONMENTAL TECHNOLOGY INC., Surrey (CA)

(72) Inventors: David A. Pasin, Vancouver (CA); Joseph Mitchell Clarkson, Vancouver (CA); Laurel L. Schafer, Vancouver (CA)

(73) Assignee: TBF ENVIRONMENTAL TECHNOLOGY INC., Surrey (CA)

( * ) Notice: Subject to any disclaimer, the term of this patent is extended or adjusted under 35 U.S.C. 154(b) by 324 days.

(21) Appl. No.: 16/652,958

(22) PCT Filed: Oct. 1, 2018

(86) PCT No.: PCT/IB2018/057613
§ 371 (c)(1),
(2) Date: Apr. 1, 2020

(87) PCT Pub. No.: WO2019/069209
PCT Pub. Date: Apr. 11, 2019

(65) Prior Publication Data
US 2020/0299525 A1 Sep. 24, 2020

Related U.S. Application Data

(60) Provisional application No. 62/566,778, filed on Oct. 2, 2017.

(51) Int. Cl.
*C09D 7/43* (2018.01)
*C09D 7/63* (2018.01)
*A01N 47/06* (2006.01)
*C07C 69/96* (2006.01)

(52) U.S. Cl.
CPC ............... *C09D 7/43* (2018.01); *A01N 47/06* (2013.01); *C07C 69/96* (2013.01); *C09D 7/63* (2018.01)

(58) Field of Classification Search
None
See application file for complete search history.

(56) References Cited

U.S. PATENT DOCUMENTS

| 2,079,629 | A | * | 5/1937 | Platt .......................... D06P 1/44 428/96 |
| 2,153,137 | A | | 4/1939 | Dickey et al. |
| 2,535,012 | A | | 12/1950 | Croxall et al. |

(Continued)

FOREIGN PATENT DOCUMENTS

| BE | 1006039 A3 | 4/1994 |
| CA | 1116835 A | 1/1980 |

(Continued)

OTHER PUBLICATIONS

JP-09165586-A—English translation (Year: 1997).*

(Continued)

*Primary Examiner* — Stefanie J Cohen
(74) *Attorney, Agent, or Firm* — Lewis Roca Rothgerber Christie LLP

(57) ABSTRACT

The present disclosure provides, in part, a solvent compound for use as a coalescent. More specifically, the present disclosure relates to VOC-exempt solvent compounds that may be used as coalescents and/or retarding solvents.

19 Claims, 8 Drawing Sheets

(56) References Cited

U.S. PATENT DOCUMENTS

| | | | |
|---|---|---|---|
| 3,632,828 A | | 1/1972 | Frevel et al. |
| 3,642,858 A | * | 2/1972 | Frevel .................. C07C 68/065 |
| | | | 558/276 |
| 3,657,310 A | | 4/1972 | Frevel et al. |
| 4,146,522 A | | 3/1979 | Heckles |
| 4,181,676 A | | 1/1980 | Buysch et al. |
| 4,238,203 A | * | 12/1980 | Jaworowski ............ B03C 3/013 |
| | | | 95/60 |
| 4,238,206 A | | 12/1980 | Hong |
| 4,390,463 A | | 6/1983 | Boden et al. |
| 5,164,497 A | | 11/1992 | King et al. |
| 5,210,322 A | | 5/1993 | King et al. |
| 5,430,170 A | | 7/1995 | Urano et al. |
| 5,430,171 A | | 7/1995 | Mitsuhashi et al. |
| 5,986,125 A | | 11/1999 | Reuter et al. |
| 6,361,709 B1 | | 3/2002 | Bauer et al. |
| 6,767,624 B2 | | 7/2004 | Bronstert |
| 7,427,406 B2 | | 9/2008 | Corbella et al. |
| 7,851,645 B2 | | 12/2010 | Ryu |
| 8,039,532 B2 | | 10/2011 | Hanaki et al. |
| 8,569,534 B2 | | 10/2013 | Ryu |
| 8,729,291 B2 | | 5/2014 | Franzke et al. |
| 9,231,274 B2 | | 1/2016 | Kinoshita et al. |
| 10,238,106 B2 | * | 3/2019 | Hahn ..................... A01N 31/02 |
| 2007/0287086 A1 | * | 12/2007 | Shinada ................ G03F 7/0007 |
| | | | 430/75 |
| 2008/0161394 A1 | | 7/2008 | Fouron et al. |
| 2008/0317694 A1 | | 12/2008 | Bruening et al. |
| 2010/0331565 A1 | | 12/2010 | Ansmann et al. |
| 2011/0137067 A1 | * | 6/2011 | Franzke ................ C07C 269/04 |
| | | | 560/26 |
| 2014/0255326 A1 | * | 9/2014 | Pasin .................... C09D 11/033 |
| | | | 106/311 |

FOREIGN PATENT DOCUMENTS

| | | |
|---|---|---|
| CA | 2940089 A1 | 9/2015 |
| CN | 101096339 A | 1/2008 |
| CN | 102959031 A | 3/2013 |
| DE | 102008052053 | 10/2008 |
| EP | 478073 A2 | 4/1992 |
| EP | 2283085 B1 | 2/2013 |
| GB | 1369716 | 10/1974 |
| GB | 2110234 A | 6/1983 |
| GB | 2472148 | 4/2014 |
| JP | 56143221 A | 11/1981 |
| JP | 09165586 A * | 6/1997 |
| JP | 2002237328 A | 8/2002 |
| JP | 2002373702 A | 12/2002 |
| JP | 201140311 A | 2/2011 |
| WO | 99/57217 | 11/1999 |
| WO | 2004074920 A1 | 9/2004 |
| WO | 2009147469 A1 | 12/2009 |
| WO | 2012010467 | 1/2012 |
| WO | 2015069854 A1 | 5/2015 |
| WO | 2015135701 A1 | 9/2015 |
| WO | 2016187798 A1 | 12/2016 |
| WO | 2016198994 | 12/2016 |
| WO | 2019069209 | 4/2019 |
| WO | 2019069210 | 4/2019 |

OTHER PUBLICATIONS

Compounds with the following CAS Nos. 705962-62-5, 705962-61-4, 705962-60-3, 705962-59-0, 193684-73-0, 193684-72-9.

Drake, Nathan L. et al., "Some Representative Carbonates and Carbo-Ethoxy Derivatives Related to Ethylene Glycol", Journal of the American Chemical Society, 1930, vol. 52, p. 3723 (http://scihub.oz/doi/10.1021/ja01372a046).

International Search Report of corresponding PCT/IB2018/057614, dated Jan. 18, 2019, 4 pages.

Written Opinion of International Searching Authority of corresponding PCT/IB2018/057614, dated Jan. 18, 2019, 5 pages.

International Search Report of PCT/IB2018/057613, dated Feb. 5, 2019, 3 pages.

Written Opinion of International Searching Authority of PCT/IB2018/057613, dated Feb. 5, 2019, 5 pages.

International Search Report and Written Opinion dated Dec. 16, 2019, issued in respect of corresponding International Patent Application No. PCT/IB2019/057015.

Rusch gen. Klaas M et al. "Reactive extraction of oilseeds with dialkyl carbonates." European Journal of Lipid Science Technology 2001, 103, 810-814.

Schaffner et al. "Organic Carbonates as Solvents in Synthesis and Catalysis." Chem. Rev. 2010, 110, 4554-4581.

Shouying Huang et al. "Recent advances in dialkyl carbonates synthesis and applications." Chem. Soc. Rev. 2015, 44, 3019.

* cited by examiner

SOLVENT COMPOUNDS FOR USE AS COALESCENTS

CROSS-REFERENCE TO RELATED APPLICATION(S)

This application is a National Phase Patent Application and claims priority to and the benefit of International Application Number PCT/IB2018/057613, filed on Oct. 1, 2018, which claims priority to and the benefit of U.S. Provisional Patent Application No. 62/566,778, filed on Oct. 2, 2017, the entire contents of all of which are incorporated herein by reference.

FIELD OF INVENTION

The present disclosure relates generally to solvent compounds that may be used as a coalescent. More specifically, the present disclosure relates to VOC-exempt solvent compounds that may be used as a coalescent or as a retarding solvent.

BACKGROUND OF THE INVENTION

Smog is known to have negative health effects on humans and the environment. A major contributor to smog formation is the release of volatile organic compounds (VOCs) which are emitted from many sources including automobile exhaust and organic solvents. VOCs are defined as "any compound of carbon, excluding carbon monoxide, carbon dioxide, carbonic acid, metallic carbides or carbonates, and ammonium carbonate, which participates in atmospheric photochemical reactions". Numerous consumer products contain VOCs as an integral component of the consumer product's function or application, such as paints or chemical coating strippers. To combat the adverse effects VOCs have on air quality in North America, agencies such as Environment and Climate Change (Canada) and the Environmental Protection Agency (United States) enforce limits on VOC content in manufacturing workplaces and consumer products. VOC emission limits in some municipalities have become even more stringent than federal standards. For example, the South Coast Air Quality Management District (SCAQMD), which regulates VOC emissions in and around Orange County, Calif., has found success in reducing smog levels by half since the 1980's despite population growth in the area. Such successes inspire increased awareness and provide support for SCAQMD's mission. While increased awareness and enforcing limits on VOC content has helped combat smog formation significantly, many sources of VOC emissions have not been curtailed. Replacing solvents that are known to contribute heavily to smog formation, due to high VOC content, with solvents that have zero or low VOC content are thus highly sought after. To further the health and safety of their constituents some agencies have also reviewed the toxicity of commonly used chemicals. In Canada, the use of solvents and paints alone corresponds to 15% of all VOC emissions, with 314.0 kilotonnes in 2014, making it the second largest contributor next to the oil and gas industry (734.1 kilotonnes in 2014). Since the VOC's used in paints and coatings are released into the environment, they should be as biodegradable and non-toxic as possible. Although some zero or low VOC solvents exist in the market place, their cost and limited applicability reduce their wide-spread use.

SUMMARY OF THE INVENTION

In one aspect, the present invention provides a compound of Formula (I):

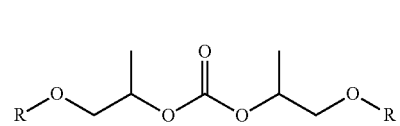

Formula (I)

where R is $C_{1-12}$ alkyl, optionally substituted from one up to the maximum number of substituents with oxygen.

In some embodiments, the compound may be:

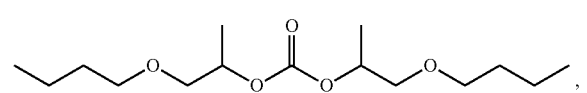

(XTR5)

or may be

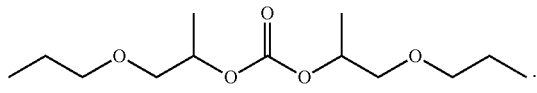

(XTR3)

In some embodiments, the compound is a coalescent, such as an inert coalescent or a film forming coalescent.

In some embodiments, the compound is a retarding solvent.

In some embodiments, the compound is a substitute for an ester alcohol.

In some embodiments, the compound is a reactive intermediate in the formation of an ester derivative for a plasticizer.

In some embodiments, the compound is a thickener.

In some embodiments, the compound is an inert ingredient in an insecticide, fungicide or rodenticide formulation.

In some aspects, the present invention provides a kit or commercial package including a compound as described herein, together with instructions for use.

In some aspects, the present invention provides a method of forming a coating on a substrate, by applying a compound of Formula (I):

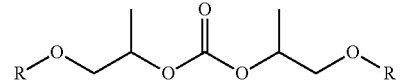

Formula (I)

where R is $C_{1-12}$ alkyl, optionally substituted from one up to the maximum number of substituents with oxygen, to the substrate. In some embodiments, the compound of Formula (I) may be provided in admixture with a paint.

Other aspects and features of the present disclosure will become apparent to those ordinarily skilled in the art upon review of the following description of specific examples.

BRIEF DESCRIPTION OF THE DRAWINGS

These and other features of the invention will become more apparent from the following description in which reference is made to the appended drawings wherein.

DETAILED DESCRIPTION

Figure 1A:
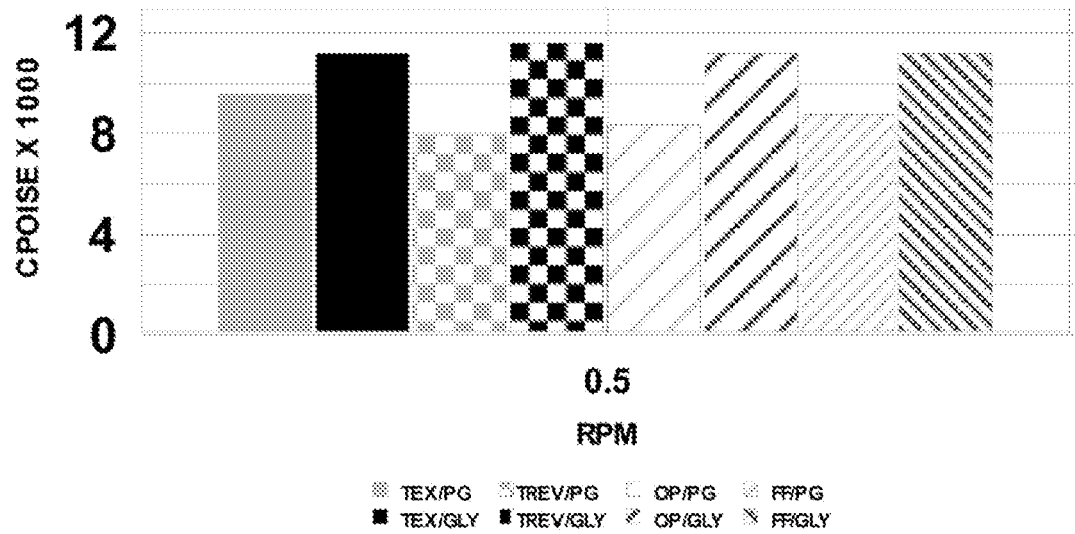
FIG. 1A is a bar graph showing the viscosity at 0.5 rpm, #4 spindle, in a PVA Flat formula.

The present disclosure provides, in part, compounds useful as coalescents.

In some embodiments, the present disclosure provides a compound of Formula (I):

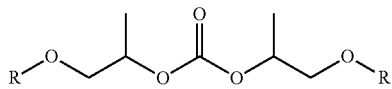

Formula (I)

where R is $C_{1-12}$ alkyl, optionally substituted from one up to the maximum number of substituents with oxygen.

The compound may be:

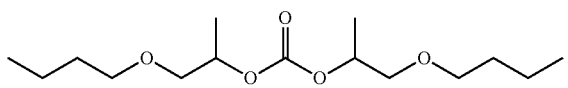 [SMILES: CCCCOCC(C)OC(=O)OC(C)COCCCC]

(referred to herein as XTR5), or may be:

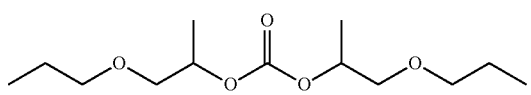 [SMILES: CCCOCC(C)OC(=O)OC(C)COCCC]

(referred to herein as XTR3).

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, 10, 11 or 12 carbon atoms, and which is attached to the rest of the molecule by a single bond. Unless stated otherwise specifically in the specification, the alkyl group may be optionally substituted by one or more oxygen atoms. Unless stated otherwise specifically herein, it is understood that the substitution can occur on any carbon of the alkyl group.

In some embodiments, a compound according to the present disclosure may have a high boiling point, for example, a boiling point over 200° C. In some embodiments, a compound according to the present disclosure may have a boiling point between about 200° C. to about 400° C., or any value therebetween.

In some embodiments, a compound according to the present disclosure may have very low vapour pressure, for example, a vapour pressure below 0.01 Pa. In some embodiments, a compound according to the present disclosure may have a vapour pressure between about 0.01 Pa to about 0.06 Pa, or any value therebetween.

In some embodiments, a compound according to the present disclosure may have a low freezing point, for example, a freezing point below −50° C. (minus 50° C.). In some embodiments, a compound according to the present disclosure may have a freezing point between about −50° C. (minus 50° C.) to about −70° C. (minus 70° C.), or any value therebetween.

In some embodiments, a compound according to the present disclosure may be hydrolytically stable, for example, as observed by placing the compounds in water and confirming their structure by $^1$H-NMR spectroscopy. By "hydrolytically stable" is meant that the compound does not exhibit substantial decomposition i.e., less than about 30% decomposition when placed in water. In some embodiments, a compound according to the present disclosure may exhibit about 0% to about 30% decomposition, or any value therebetween, when placed in water.

In some embodiments, a compound according to the present disclosure may break down into carbon dioxide and water. In some embodiments, a compound according to the present disclosure may break down into carbon dioxide and water when exposed to air at ambient room temperature. In some embodiments, a compound according to the present disclosure may break down into carbon dioxide and water when exposed to air at a temperature >−1° C. (minus 1° C.).

In some embodiments, a compound according to the present disclosure may have high hydrophobicity, for example, does not readily dissolve in water. Hydrophobicity may be measured using standard techniques, for example, by determining the solubility constant of the compound in water. By "high hydrophobicity" is meant a solubility constant of 99% or more. In some embodiments, a compound according to the present disclosure may have a hydrophobicity (i.e., solubility constant) between about 0% to about 99.9%, or any value therebetween.

In some embodiments, a compound according to the present disclosure may have high efficiency of coalescence, for example, in comparison to typically used coalescents, such as Texanol™ (2-methyl-, 3-hydroxy-2,2,4-trimethylpentyl ester), Film Former IBT (2,2,4-Trimethyl-1,3-Pentanediol Monoisobutyrate; isobutyric acid, ester with 2,2,4-trimethyl-1,3-pentanediol) or Opti Film Enhancer 400, when used as a direct replacement.

In some embodiments, a compound according to the present disclosure may not be classified as hazardous air pollutants (HAPs), or as containing Saturates, Asphaltenes, Resins and Aromatics (SARA). In some embodiments, a compound according to the present disclosure may be VOC-exempt. In some embodiments, a compound according to the present disclosure may reduce the overall VOC of a composition in which it is present. For example, when a compound according to the present disclosure is provided in combination with a VOC-containing compound, the overall VOC of the combination may be reduced. By "about" is meant a variance (plus or minus) from a value or range of 5% or less, for example, 0.5%, 1%, 1.5%, 2.0%, 2.5%, 3.0%, 3.5%, 4.0%, 4.5%, 5.0%, etc.

By "about" is meant a variance (plus or minus) from a value or range of 5% or less, for example, 0.5%, 1%, 1.5%, 2.0%, 2.5%, 3.0%, 3.5%, 4.0%, 4.5%, 5.0%, etc.

In some embodiments, a compound according to the present disclosure may have low toxicity as determined, for example by one or more of oral $LD_{50}$ on rats, biodegradability, teratogenicity, carcinogenicity and/or hepatic and renal toxicity measurements, which can be determined using standard methods. In some embodiments, a compound according to the present disclosure may contain reagents classified as non-carcinogenic. A compound according to the present disclosure may have an $LD_{50}$ of 5000 mg/kg or more.

In some embodiments, a compound according to the present disclosure may be substantially anhydrous, for example, containing less than 0.05 wt % water. In alternative embodiments, a compound according to the present disclosure may contain less than 500 ppm of water.

In some embodiments, a compound according to the present disclosure may have a purity of, for example, at least 99.5%, for example, at least 99.6%, 99.7%, 99.8%, 99.9%, or 100%.

In some embodiments, a compound according to the present disclosure may be useful as a coalescent.

In some embodiments, a compound according to the present disclosure may be useful as an inert coalescent for, for example, latex or acrylic paints or coatings.

In some embodiments, a compound according to the present disclosure may offer superior coalescing performance in a wide variety of conditions including climate and substrates of different compositions and porosity.

In some embodiments, a compound according to the present disclosure may be useful as a retarding solvent in, for example, coil coatings and high-bake enamel, oil field, floor polish, and/or wood preservatives formulations. By "retarding solvent" is meant a solvent capable of slowing down the drying time of a film to, for example, enhance film appearance and coverage.

In some embodiments, a compound according to the present disclosure may be useful as a substitute for an ester alcohol when used, for example, to coalesce a film, enhance thickening efficiency and/or act as a retarding solvent for use in coil coatings and/or high-bake enamels.

In some embodiments, a compound according to the present disclosure may be useful as a reactive intermediate in the formation of ester derivatives for a plasticizer.

In some embodiments, a compound according to the present disclosure may be useful as a film forming coalescent in a variety of coatings.

In some embodiments, a compound according to the present disclosure may improve the gloss of a paint and/or coating.

In some embodiments, a compound according to the present disclosure may improve the integrity and/or durability of a paint and/or coating.

In some embodiments, a compound according to the present disclosure may improve the scrub resistance of a paint and/or coating.

In some embodiments, a compound according to the present disclosure may improve the ability of a paint and/or coating to form a durable film at less than −1° C. (minus 1° C.).

In some embodiments, a compound according to the present disclosure may be useful to: create a film of high integrity; improve the overall performance characteristics of a paint or coating; allow film coalescence at low temperatures (for example, about 5° C.; enhance colour development of a film; improve gloss of a film; improve washability of a film; improve scrub resistance of a film; increase the thermal torsional and tensile strength of a film; resist mud cracking of a film; and/or provide superior adhesion properties of a film.

In some embodiments, a compound according to the present disclosure may enhance the thickening efficiency of various associative thickeners, such as Bentonite, HEC (Hydroxy Ethyl Cellulose) or HEUR (Hydrophobe-modified Ethoxylated Urethane), and thereby improve the practical viscosity of a paint or coating.

In some embodiments, a compound according to the present disclosure may be widely useful as a general industrial primer, intermediate and/or topcoat, as automotive refinish and/or OEM, wood primer and/or topcoats, marine, can and/or coil, printing ink (for example, lithographic and/or letterpress) and/or oil field chemical (such as drilling mud, frothing agent, ore flotation) formulae.

In some embodiments, a compound according to the present disclosure may be used as an inert ingredient, which is permitted for non-food use contact, in the formulation of an insecticides, a fungicide and/or a rodenticide.

A compound according to the present disclosure may be prepared as described herein, or using techniques based on, or similar to, those known in the art, such as those referenced in U.S. Pat. No. 5,986,125, 4,181,676, 3,657,310, 3,642,858, or 3,632,828.

Example 1

Synthesis of bis(1-butoxypropan-2-yl) carbonate (TreviSol, XTR5)

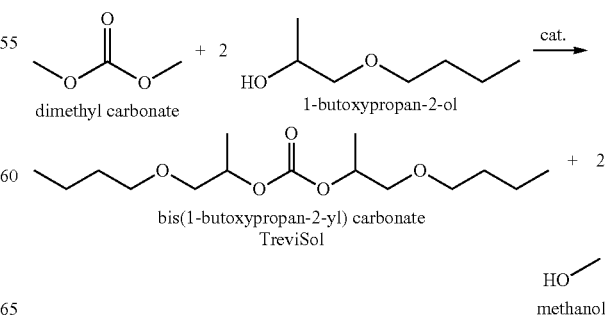

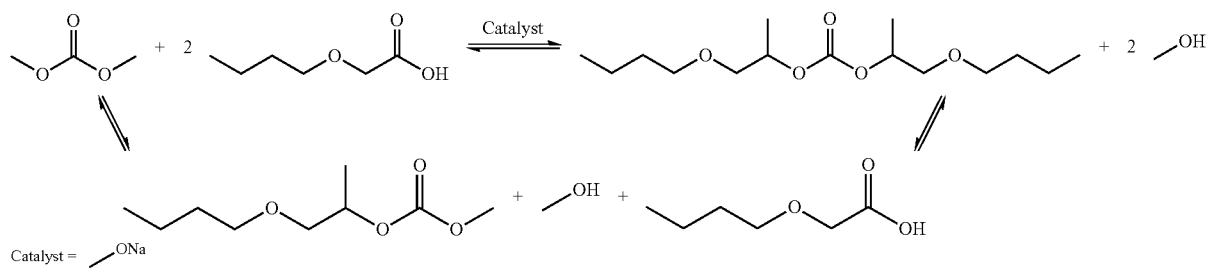

Ether Bi-Product Formation

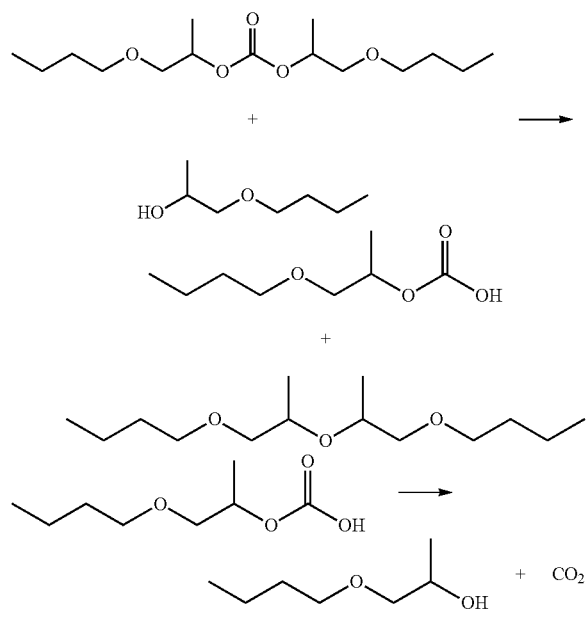

The alcohol 1-butoxypropan-2-ol, CAS #5131-66-8 (1.0 L) was put in a 2 L round bottom flask. The flask was then charged with sodium methanolate (~1.5 g) and hexanes (~350 mL). Dimethyl carbonate (270 mL) is then added. Boiling stones (3-10) are added to prevent bumping during the reaction. A Dean Stark apparatus is attached to the round bottom flask, and 15 mL of distilled water was added to the trap, the rest of the trap volume was filled with hexanes. A condenser is attached to the top of the Dean Stark apparatus. The reaction was then heated gently until the distillate temperature is 53(±3)° C. As the distillate condenses into the Dean Stark trap the methanol formed from the transesterification reaction separates to the bottom of the trap. The trap was refreshed when the bottom layer of the Dean stark trap was approximately half full. The reaction was monitored by taking $^1$H-NMR of the reaction mixture and is continued until the dimethyl carbonate was completely consumed and less than 5% of the unsymmetric organic carbonate intermediate was observed, the hexanes are then distilled off. The reaction was then cooled and filtered through a 1-3 cm layer of diatomaceous earth and transferred to another 2 L round bottom flask. The crude material is then distilled under vacuum (currently do not know the pressure) and when the distillate reaches 130° C., it was collected and analyzed for purity. The typical yield was 450 mL of the desired product.

The physical/chemical properties of bis(1-butoxypropan-2-yl) carbonate (TreviSol, XTR5) were determined to be as follows:

| | |
|---|---|
| Upper Explosive Limit (UEL %) | 7.04 |
| Lower Explosive Limit (LEL %) | 0.40 |
| Auto Ignition Temp (° C.) | 300 (572° F.) |
| Flashpoint (° C.) (PMCC) | 143.3 (290° F.) |
| Boiling Point (° C.) | 285 (545° F.) |
| Molecular Weight (g/mol) | 290.4 |
| Density (g/mL @ 20° C.) | 0.951 (7.94 lb/gal) |
| Viscosity (cP @ 25° C.) | 0.58 |
| Specific Gravity (@15.5°) | 0.956 |
| Solubility in $H_2O$ (g/mL @ 25° C.) | Insoluble |
| Vapour Pressure (mm Hg @ 25° C.) | 0.005 |
| Evaporation Rate (n-Butyl Acetate = 1) | 0.0004 |
| Vapour Density (mm Hg Air = 1) | 0.95 |
| Freezing Point | <−60 (<−76° F.) |
| Purity (Wt % Min) | 99.5% |
| Water Content (ppm) | <0.01 |
| Colour (Alpha, max) | 10 (Clear) |
| Volatility (%) | 100 |
| TGA Weight Loss (Ambient 115-240° C.) | 97.94% |
| Heat of Combustion (Blu/lb) | −13000 |
| (Kcal/Kg) | −7100 |
| (Kj/mol) | −8600 |
| Heat of Vaporization (Blu/lb) | 64 |
| (cal/g) | 35 |
| (Kj/mol) | 43 |
| Partial Coefficient (Range) | 0.7-2.0 |
| VOC (g/L) | 0 |

Texanol Solubility: Soluble

Water Solubility: Not Soluble

Odor: Pleasant Odor

Clarity: Clear

Evaporation Rate: Slow and Close to Texanol

Bis(1-butoxypropan-2-yl) carbonate (TreviSol, XTR5) was used as a direct replacement for other typical coalescents, such as, Texanol™, as follows.

| 7.5% of Coalescent in Acrylic Polymer (Raycryl 1526 from Specialty Polymers Tg = 25° C.) | | |
|---|---|---|
| | Texanol | XTR5 |
| Formula | | |
| Raycryl 1526 (50% Solid) | 100 | 100 |
| Coalescent | 3.75 | 3.75 |
| Physical Properties | | |
| Mixing Ease | Not Easy, Needs speed to dissolve | Not Easy, Needs speed to dissolve |
| Compatibility | Compatible | Compatible |
| Film Clarity | Clear | Clear |

7.5% of Coalescent in Acrylic Polymer (Raycryl 1526 from Specialty Polymers Tg = 25° C.)

|  | Texanol | XTR5 |
| --- | --- | --- |
| Film Gloss | Glossy | Glossy |
| Film Flexibility, Softness | The same | The same |
| Touch Dry (3 mils Wet Film) | 45 min. | 45 min. |

XTR5 v.s. Texanol in Raycryl 1526 (Tg = 25° C.) Acrylic Emulsion Polymer from Specialty Polymers

| Raw Materials | Texanol | XTR5 |
| --- | --- | --- |
| Water | 180.0 | 180.0 |
| Cellulosic Thickener | 3.0 | 3.0 |
| Co-Dispersant | 0.5 | 0.5 |
| Anionic Disperser | 8.0 | 8.0 |
| Non-ionic Surfactant | 3.0 | 3.0 |
| Oil Base Defoamer | 2.0 | 2.0 |
| Titanium Dioxide | 150.0 | 150.0 |
| Calcium Carbonate | 100.0 | 100.0 |
| Raycryl 1526 (50%) | 450.0 | 450.0 |
| Propylene Glycol | 15.0 | 15.0 |
| Texanol | 17.0 | — |
| XTR | — | 17.0 |
| Silicone Base Defoamer | 2.0 | 2.0 |
| HEAT Associated Thickener | 13.5 | 13.5 |
| HEUR Associated Thickener | 4.5 | 4.5 |
| Total | 948.5 | 948.5 |

Physical Properties

|  | Texanol | XTR5 |
| --- | --- | --- |
| Polymer Solid % | 23.7 | 23.7 |
| Texanol or XTR Solid Polymer % | 7.5 | 7.5 |
| Specific Gravity g/cm3 | 1.25 | 1.25 |
| Weight Solid % | 51.91 | 51.91 |
| Volume Solid %~VOC | 40.91 | 40.91 |
| (Without Water) g/L | 95.0 | 45.0 |

Test Results

| Paint Properties | Texanol | XTR5 |
| --- | --- | --- |
| Viscosity | 90 KU | 90 KU |
| Fineness of Grind | 40-45 micron | 40-45 micron |
| Hide at 5.0 mils | The same | The same |
| Touch Dry @ 20° C. | 45 minutes | 45 minutes |
| Gloss @ 60 Degree | ~15 | ~15 |
| Flexibility | The same | The same |

XTR5 vs Texanol in Raycryl 1001 (Tg = 36° C.) Acrylic Emulsion Polymer from Specialty Polymers

| Raw Materials | Texanol | XTR5 |
| --- | --- | --- |
| Water | 160.0 | 160.0 |
| Cellulosic Thickener | 2.0 | 2.0 |
| Co-Dispersant | 0.5 | 0.5 |
| Anionic Dispersing Agent | 8.0 | 8.0 |
| Oil Base Defoamer | 2.0 | 2.0 |
| Titanium Dioxide | 200.0 | 200.0 |
| Raycryl 1001 (46%) | 440.0 | 440.0 |
| Texanol | 18.0 | — |
| XTR | — | 18.0 |
| HEUR Associative Thickener | 4.0 | 4.0 |
| Silicone Defoamer | 1.0 | 1.0 |
| Total | 935.5 | 935.5 |

Physical Properties

|  | Texanol | XTR5 |
| --- | --- | --- |
| Polymer Solid % | 21.6 | 21.6 |
| Texanol ot XTR on Solid Polymer % | 9.0 | 9.0 |
| Specific Gravity g/cm3 | 1.32 | 1.32 |
| Weight Solid % | 54.6 | 54.6 |
| Volume Solid % | 41.1 | 41.1 |
| VOC (Without Water) g/L | 54.6 | 1.5 |

Test Results

| Coating Properties | Texanol | XTR5 |
| --- | --- | --- |
| Viscosity | 95 KU | 95 KU |
| Fineness of Grind | 45-50 micron | 45-50 micron |
| Hide at 5.0 mils | The same | The same |
| Touch Dry @ 20° C. | 35 minutes | 35 minutes |
| Gloss @ 60 Degree | ~20 | ~20 |
| Flexibility | The same | The same |

XTR5 vs Texanol in EPS 2708 (MFFT = 20° C.) Acrylic Emulsion Polymer from EPS

| Raw Materials | Texanol | XTR5 |
| --- | --- | --- |
| Water | 220.0 | 220.0 |
| Cellulosic Thickener | 3.0 | 3.0 |
| Co-Dispersant | 0.5 | 0.5 |
| Anionic Dispersing Agent | 8.0 | 8.0 |
| Non-ionic Surfactant | 3.0 | 3.0 |
| Oil Base Defoamer | 2.0 | 2.0 |
| Titanium Dioxide | 50.0 | 50.0 |
| Nepheline Syenite Filler | 150.0 | 150.0 |
| Calcium Carbonate | 150.0 | 150.0 |
| EPS 2708 (50.0%) | 360.0 | 360.0 |
| Propylene Glycol | 15.0 | 15.0 |
| Texanol | 15.0 | — |
| XTR | — | 15.0 |
| Low VOC Coalescent | 5.0 | 5.0 |
| HEUR Associative Thickener | 16.0 | 16.0 |
| Oil Base Defoamer | 2.0 | 2.0 |
| Total | 999.5 | 999.5 |

|  | Texanol | XTR5 |
| --- | --- | --- |
| Physical Properties |  |  |
| Polymer Solid % | 18.0 | 18.0 |
| Texanol or XTR on Solid Polymer % | 11.1 | 11.1 |
| Specific Gravity g/cm3 | 1.33 | 1.33 |
| Weight Solid % | 54.5 | 54.5 |
| Volume Solid % | 41.0 | 41.0 |
| VOC (Without Water) g/L | 103.3 | 59.6 |

| | Texanol | XTR5 |
|---|---|---|
| Test Results | | |
| Coating Properties | | |
| Viscosity | 95 KU | 95 KU |
| Fineness of Grind | 45-50 micron | 45-50 micron |
| Hide at 5.0 mils | The same | The same |
| Touch Dry @ 20° C. | 30 minutes | 30 minutes |
| Gloss @ 60 Degree | ~15 | ~15 |
| Flexibility | The same | The same |

The results indicated that XTR5 performed the same as the tested coalescent, in terms of dry time, gloss, brush roll application and film integrity.

Example 2

Synthesis of bis(1-propoxypropan-2-yl) carbonate (XTR3)

XTR3 was prepared as set forth in Example 1, herein, except 1-propoxypropan-2-ol, CAS #1569-01-3, was used in place of 1-butoxypropan-2-ol.

Example 3

Results of bis(1-butoxypropan-2-yl) carbonate (TreviSol, XTR5) Tests

Bis(1-butoxypropan-2-yl) carbonate (TreviSol, XTR5) was tested in a number of water-based flat paints, as follows. Water was added to a container and the additives were added. The container was placed under a high speed disperser and mixed under slow speed. Natrosol™ hydroxyethylcellulose was added slowly and allowed to mix for 10 minutes increasing speed as needed. The pigments were then added, slowly increasing speed and water as needed. After the pigments were added, the speed was increased to about 2800 rpms. After 10 to 15 minutes the speed was reduced to about 1000 rpms. The latex was added slowly into the vortex. The rest of the water and other additives (depending on the formulation) were then added and allowed to mix for 5 minutes.

The testing was conducted as follows. A 3 wet mil drawdown was made on a opacity chart. Dry time was done by putting the opacity chart under a Gardco Ultracycle RHT 5022 dry time tester and letting it run until the coating was dry. The optical properties were done using the same opacity chart after 24 hours dry time. The L* a* b* were read using a X-rite RM200QC. The gloss was measured using aETB-0833 glossmeter.

In some tests, bis(1-butoxypropan-2-yl) carbonate (TreviSol, XTR5) was substituted for propylene glycol to evaluate its effectiveness in replacing propylene glycol to create a lower VOC and lower toxicity material. The results indicated that replacement of bis(2-ButoxyEthyl Carbonate) for propylene glycol resulted in far lower or zero (0) VOC materials. Parameters such as dry time, gloss, solids %, and opacity, which are important in measuring the qualities of a coating, were not adversely affected.

In the various tests, the following abbreviations were used:
TEX: Texanol™
PG: Propylene Glycol
GLY: GlykoSol (Bis(2-ButoxyEthyl Carbonate), XBC4)
TREV, TER or TRV: TreviSol (bis(1-butoxypropan-2-yl) carbonate)
OP: Optifilm™ 400, and
FF: Film Former IBT.

Example 4

PVA Flat Formula

Table 1 shows materials and combinations tested in a PVA flat formula.

TABLE 1

| PVA Flat Latex Formula | | | | | | | | |
|---|---|---|---|---|---|---|---|---|
| | A | B | C | D | E | F | G | H |
| WATER | | | | 397.5 | | | | |
| NATROSOL 330 PLUS | | | | 5.0 | | | | |
| KTPP | | | | 1.8 | | | | |
| COLLOIDS 226 | | | | 8.0 | | | | |
| IGEPAL CO-610 | | | | 4.0 | | | | |
| COLLOIDS 691 | | | | 3.0 | | | | |
| TIO2(R-706) | | | | 91.1 | | | | |
| HUBERCARB 325G | | | | 235.5 | | | | |
| KAMIN 70C | | | | 100.0 | | | | |
| UCAR 379 | | | | 250.0 | | | | |
| TEXANOL | 10.0 | 10.0 | | | | | | |
| OPTIFILM 400 | | | | | 10.0 | 10.0 | | |
| TREVISOL | | | 10 | 10 | | | | |
| UCAR FILM IBT | | | | | | | 10.0 | 10.0 |
| PROPYLENE GLYCOL | 23.3 | | 23.3 | | 23.3 | | 23.3 | |
| GLYKOSOL | | 23.3 | | 23.3 | | 23.3 | | 23.3 |

The results for the viscosities (PVA flat) are shown in Table 2.

TABLE 2

| CQ217016 PVA FLAT | | | | | | | | | | | | | | | |
| --- | --- | --- | --- | --- | --- | --- | --- | --- | --- | --- | --- | --- | --- | --- | --- |
| | 0.5 | 1 | 2.5 | 5 | 10 | 20 | 50 | 100 | 50 | 20 | 10 | 5 | 2.5 | 1 | 0.5 |
| TEX/PG | 9600 | 7000 | 4240 | 3000 | 2120 | 1510 | 1016 | 774 | 1008 | 1470 | 2000 | 2840 | 4000 | 6200 | 8800 |
| TEX/GLY | 11200 | 7800 | 4880 | 3360 | 2340 | 1650 | 1056 | 760 | 1040 | 1600 | 2260 | 3160 | 4640 | 7200 | 10000 |
| TREV/PG | 8000 | 6000 | 3760 | 2600 | 1840 | 1330 | 892 | 670 | 888 | 1310 | 1800 | 2520 | 3680 | 6000 | 9200 |
| TREV/GLY | 11600 | 8400 | 5200 | 3520 | 2440 | 1710 | 1088 | 778 | 1068 | 1650 | 2320 | 3280 | 4800 | 7600 | 11200 |
| OP/PG | 8400 | 6000 | 3760 | 2640 | 1880 | 1350 | 904 | 680 | 896 | 1330 | 1820 | 2520 | 3600 | 5800 | 8800 |
| OP/GLY | 11200 | 7800 | 4960 | 3400 | 2380 | 1700 | 1116 | 820 | 1108 | 1680 | 2320 | 3240 | 4640 | 7400 | 10400 |
| FF/PG | 8800 | 6200 | 3920 | 2800 | 1980 | 1430 | 964 | 734 | 960 | 1410 | 1920 | 2680 | 3840 | 6000 | 9600 |
| FF/GLY | 11200 | 7800 | 4960 | 3400 | 2380 | 1700 | 1116 | 820 | 1108 | 1680 | 2320 | 3240 | 4640 | 7400 | 10400 |

The results for different parameters (PVA flat) are shown in Table 3.

TABLE 3

| | TEX PG CONTROL | TEX GLY | TREV PG | TREV GLY | OP PG | OP GLY | FF PG | FF GLY |
| --- | --- | --- | --- | --- | --- | --- | --- | --- |
| 60 Deg Gloss | 0.7 | 1.1 | 1.3 | 1.4 | 1.4 | 1.4 | 1.6 | 1.2 |
| L* | 95.7 | 95.7 | 95.6 | 95.5 | 95.6 | 95.6 | 95.7 | 95.7 |
| a* | −0.9 | −0.9 | −0.9 | −0.9 | −0.9 | −0.9 | −0.9 | −0.9 |
| b* | 1.5 | 1.5 | 1.4 | 1.5 | 1.5 | 1.5 | 1.5 | 1.4 |
| Opacity (Y) | 88.6 | 89.3 | 88.6 | 88.8 | 87.8 | 87.8 | 88.4 | 88.1 |
| VOC (CALCULATED) (g/l) | 104.8 | 33.9 | 76.1 | 0.0 | 105.2 | 34.0 | 105.1 | 34.0 |
| DRY TIME MINUTES | 22 | 22 | 20 | 25 | 20 | 25 | 22 | 28 |
| SOLIDS (2 HRS) | 52.11% | 53.75% | 52.78% | 53.41% | 51.97% | 53.65% | 52.09% | 53.01% |
| SOLIDS (24 HRS) | 51.89% | 52.52% | 51.89% | 52.21% | 51.60% | 52.58% | 51.69% | 51.96% |
| SOLIDS CALCULATED | 51.35% | 51.41% | 51.35% | 51.41% | 51.35% | 51.41% | 51.35% | 51.41% |

Figure 1B:
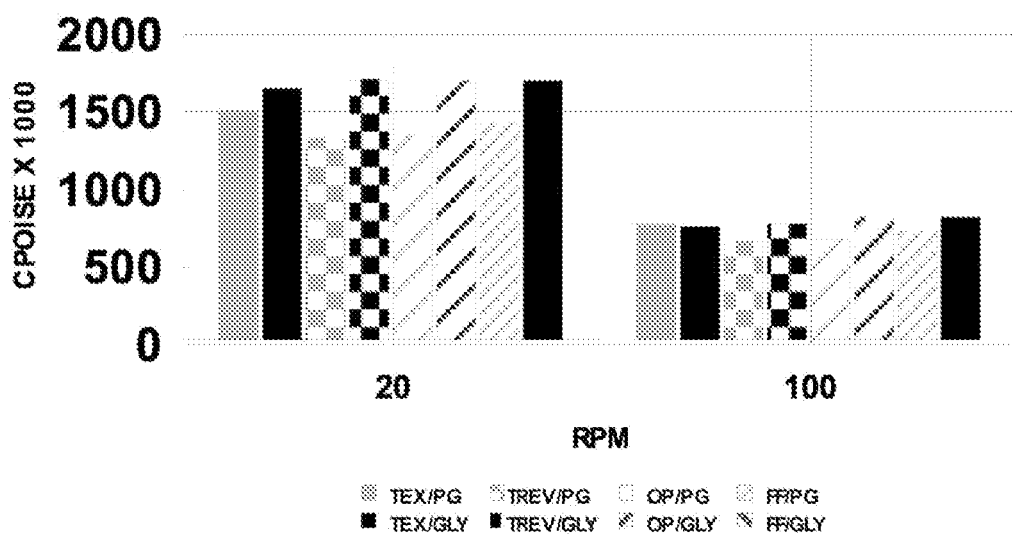
FIG. 1B is a bar graph showing the viscosity at 20 rpm and 100 rpm, #4 spindle, in a PVA Flat formula.
Figure 1C:
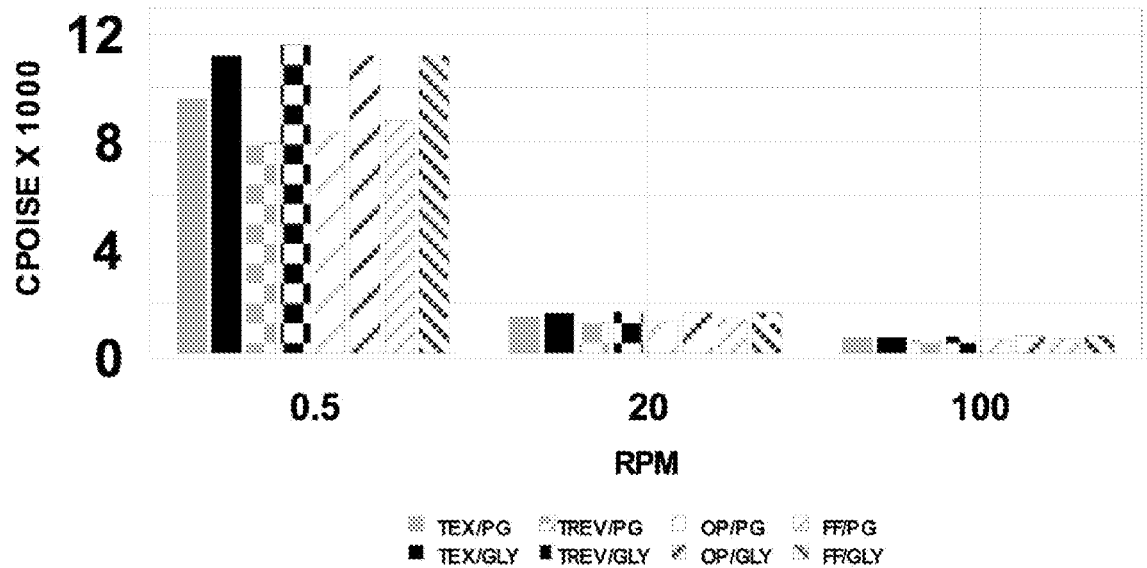
FIG. 1C is a bar graph showing the viscosity at 0.5 rpm, 20 rpm and 100 rpm, #4 spindle, in a PVA Flat formula.

FIGS. 1A-C show differences in viscosity, depending on the components. The tests were performed on a Brookfield viscometer and demonstrate that different components have different effects in thickness or viscosity within a formula.

Example 5

PVA Semi Gloss Formula

Bis(2-ButoxyEthyl Carbonate) was tested in a number of water-based flat paints, as set out in Example 3. Table 4 shows materials and combinations tested in a PVA semi gloss formula.

TABLE 4

| | A | B | C | D | E | F | G | H |
| --- | --- | --- | --- | --- | --- | --- | --- | --- |
| WATER | | | | 292.0 | | | | |
| COLLOIDS 226 | | | | 6.6 | | | | |
| IGEPAL CO-630 | | | | 2.5 | | | | |
| AMP-95 | | | | 3.3 | | | | |
| COLLIDS 691 | | | | 4.9 | | | | |
| TIO2(R-706) | | | | 200.0 | | | | |
| HUBERCARB 3G | | | | 90.0 | | | | |
| NATROSOL PLUS | | | | 2.5 | | | | |
| ENCOR 379G | | | | 400.2 | | | | |
| ACRYSOL TT-935 | | | | 1.6 | | | | |
| AMMONIA | | | | 1.6 | | | | |
| TEXANOL | 14.0 | 14.0 | | | | | | |
| OPTIFILM 400 | | | | | 14.0 | 14.0 | | |
| TREVISOL | | | 14.0 | 14.0 | | | | |
| UCAR FILM IBT | | | | | | | 14.0 | 14.0 |
| PROPYLENE GLYCOL | 24.7 | | 24.7 | | 24.7 | | 24.7 | |
| GLYKOSOL | | 24.7 | | 24.7 | | 24.7 | | 24.7 |

The results for the viscosities (PVA Semi Gloss) are shown in Table 5.

TABLE 5

| CQ217015 PVA SEMIGLOSS | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 10000 | 6700 | 3760 | 2440 | 1590 | 1055 | 634 | 447 | 618 | 1005 | 1470 | 2240 | 3400 | 5800 | 8800 |
| TEX/GLY | 12400 | 8200 | 4640 | 2920 | 1910 | 1255 | 748 | 517 | 736 | 1220 | 1830 | 2780 | 4320 | 7800 | 12200 |
| TREV/PG | 7200 | 5000 | 3080 | 2040 | 1360 | 925 | 560 | 392 | 546 | 880 | 1280 | 1880 | 2840 | 4800 | 7400 |
| TREV/GLY | 12400 | 8100 | 4400 | 2740 | 1780 | 1175 | 698 | 486 | 696 | 1155 | 1730 | 2620 | 4120 | 7300 | 11800 |
| OP/PG | 7800 | 5300 | 3080 | 1980 | 1320 | 880 | 536 | 383 | 492 | 845 | 1230 | 1860 | 2720 | 4700 | 7200 |
| OP/GLY | 11400 | 7300 | 4080 | 2620 | 1700 | 1120 | 670 | 468 | 670 | 1100 | 1640 | 2480 | 3840 | 6800 | 10400 |
| FF/PG | 10400 | 6700 | 3720 | 2320 | 1530 | 1030 | 616 | 436 | 606 | 975 | 1440 | 2160 | 3320 | 5800 | 9400 |
| FF/GLY | 11400 | 7600 | 4240 | 2720 | 1780 | 1175 | 504 | 493 | 702 | 1155 | 1730 | 2620 | 4080 | 7300 | 11400 |

The results for different parameters (PVA Semi Gloss) are shown in Table 6.

TABLE 6

| | A TEX PG CONTROL | B TEX GLY | C TREV PG | D TREV GLY | E OP PG | F OP GLY | G FF PG | H FF GLY |
|---|---|---|---|---|---|---|---|---|
| 20 Deg Gloss | 4.1 | 4.0 | 3.9 | 6.2 | 5.3 | 5.5 | 3.4 | 3.4 |
| 60 Deg Gloss | 26.0 | 25.8 | 25.5 | 33.1 | 27.0 | 31.3 | 24.2 | 24.0 |
| L* | 97.0 | 96.8 | 96.8 | 96.9 | 96.4 | 96.9 | 96.7 | 96.8 |
| a* | −0.8 | −0.8 | −0.8 | −0.8 | −0.8 | −0.8 | −0.8 | −0.7 |
| b* | 0.7 | 0.8 | 0.7 | 0.8 | 0.6 | 0.8 | 0.7 | 0.7 |
| Opacity (Y) | 95.5 | 95.9 | 95.9 | 96.4 | 96.4 | 96.2 | 96.6 | 96.9 |
| DRY TIME MINUTES | 45.0 | 20.0 | 25.0 | 45.0 | 30.0 | 25.0 | 25.0 | 25.0 |
| KU VISC | 70.0 | 71.0 | 69.0 | 71.0 | 69.0 | 71.0 | 69.0 | 71.0 |
| VOC (CALCULATED) | 117.2 | 45.8 | 78.6 | 0.0 | 117.8 | 46.0 | 117.6 | 49.9 |

Figure 2A:
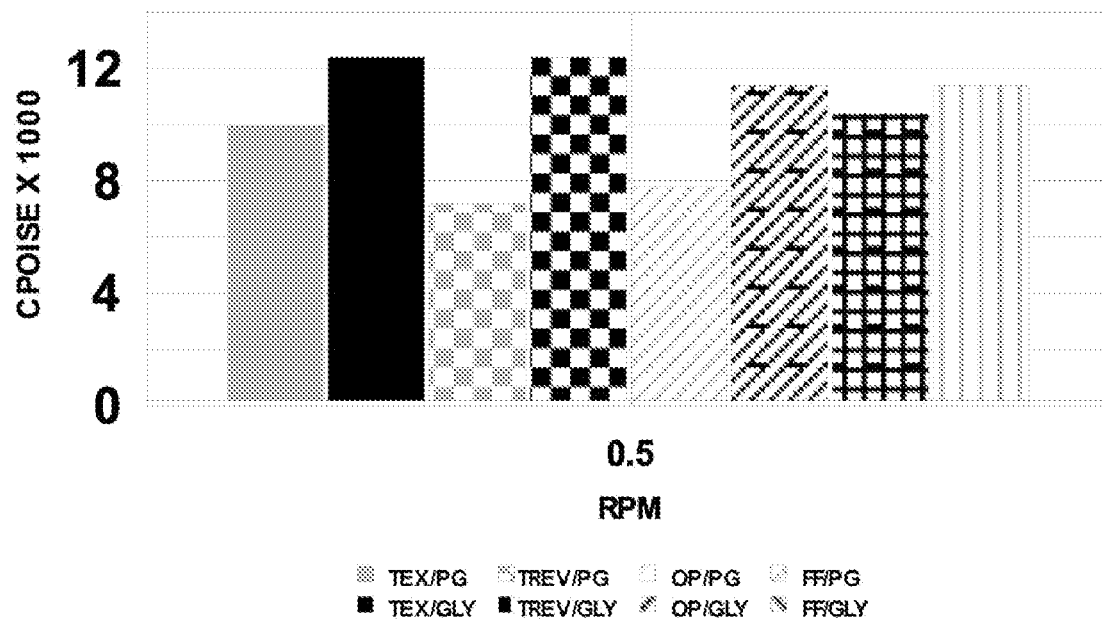
FIG. 2A is a bar graph showing the viscosity at 0.5 rpm in a PVA Semi Gloss formula.
Figure 2B:
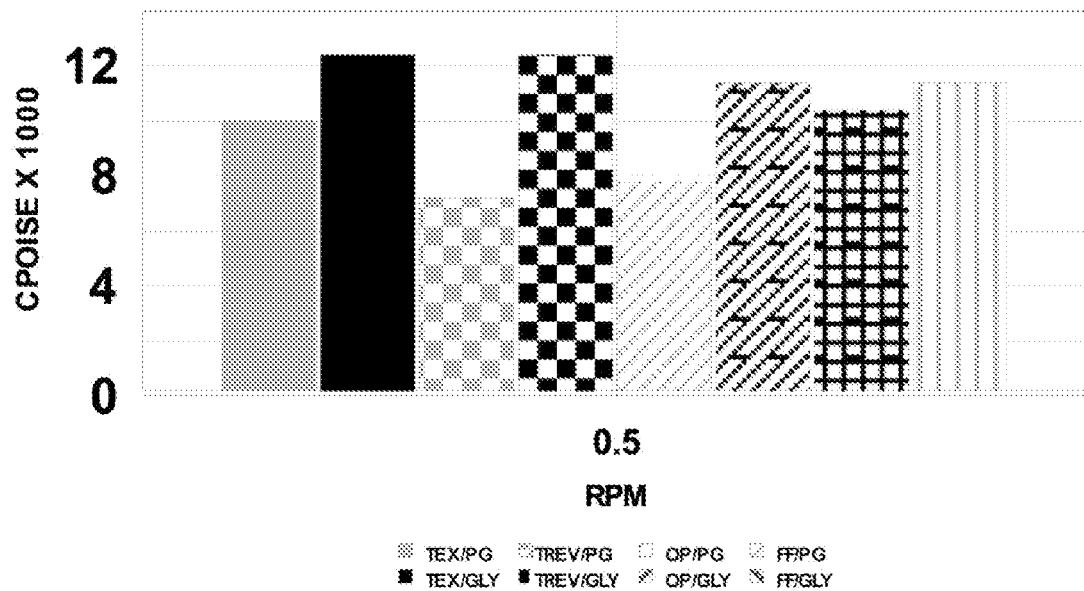
FIG. 2B is a bar graph showing the viscosity at 0.5 rpm in a PVA Semi Gloss formula.
Figure 2C:
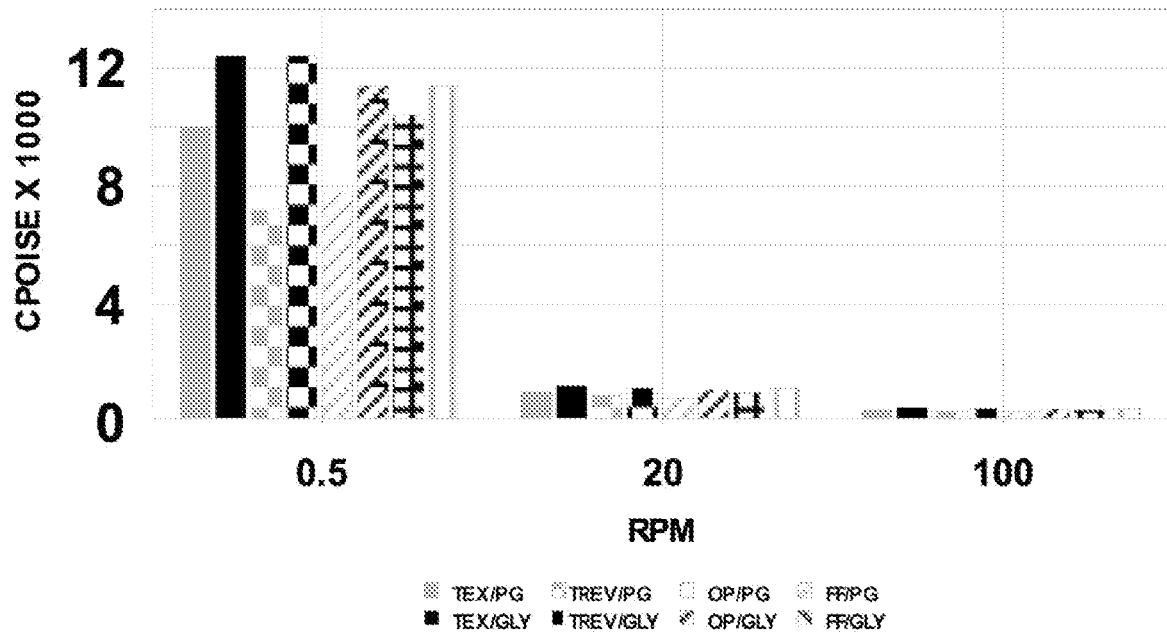
FIG. 2C is a bar graph showing the viscosity at 0.5 rpm, 20 rpm and 100 rpm in a PVA Semi Gloss formula.

FIGS. 2A-C show differences in viscosity, depending on the components. The tests were performed on a Brookfield viscometer and demonstrate that different components have different effects in thickness or viscosity within a formula.

Example 6

EVA Flat Formula

Bis(2-ButoxyEthyl Carbonate) was tested in a number of water-based flat paints, as set out in Example 3. Table 7 shows materials and combinations tested in an EVA flat formula.

TABLE 7

| | A | B | C | D | E | F | G | H |
|---|---|---|---|---|---|---|---|---|
| WATER | | | | 324.9 | | | | |
| COLLOIDS 226 | | | | 3.0 | | | | |

TABLE 7-continued

| | A | B | C | D | E | F | G | H |
|---|---|---|---|---|---|---|---|---|
| IGEPAL CO-630 | | | | 2.0 | | | | |
| AMP-95 | | | | 4.5 | | | | |
| COLLIDS 691 | | | | 5.0 | | | | |
| TIO2(R-706) | | | | 150.0 | | | | |
| HUBERCARB G325 | | | | 250.0 | | | | |
| NATROSOL PLUS | | | | 6.0 | | | | |
| KAMIN 70C | | | | 150.0 | | | | |
| ECOVAE 405 | | | | 310.0 | | | | |
| TEXANOL | 5.0 | 5.0 | | | | | | |
| OPTIFILM 400 | | | | | 5.0 | 5.0 | | |
| TREVISOL | | | 5.0 | 5.0 | | | | |
| UCAR FILM IBT | | | | | | | 5.0 | 5.0 |
| PROPYLENE GLYCOL | | 5.0 | | 5.0 | | 5.0 | | 5.0 |

The results for the viscosities (EVA flat) are shown in Table 8.

TABLE 8

| CQ217023 EVA FLAT | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 46400 | 28800 | 15360 | 9680 | 6360 | 4280 | 2616 | 1892 | 2576 | 4120 | 6080 | 9200 | 14400 | 27200 | 44800 |
| TEX/GLY | 50400 | 31600 | 17120 | 10720 | 7000 | 4580 | 2896 | 2036 | 2792 | 4480 | 6680 | 10080 | 15840 | 29600 | 48800 |
| TREV/PG | 47200 | 29200 | 15520 | 9840 | 6400 | 4240 | 2536 | 1844 | 2520 | 4040 | 6000 | 9120 | 14560 | 27200 | 44800 |
| TREV/GLY | 45600 | 29220 | 15680 | 10160 | 6680 | 4460 | 2704 | 1948 | 2680 | 4300 | 6360 | 9600 | 15040 | 28400 | 47200 |
| OP/PG | 45600 | 28400 | 15200 | 9600 | 6240 | 4140 | 2528 | 1796 | 2472 | 3960 | 5840 | 8880 | 14080 | 26000 | 44000 |
| OP/GLY | 48000 | 30800 | 16640 | 10640 | 6920 | 4620 | 2824 | 1996 | 2736 | 4360 | 6440 | 9760 | 15200 | 28400 | 47200 |
| FF/PG | 48800 | 30000 | 16320 | 10320 | 6760 | 4500 | 2720 | 1952 | 2640 | 4220 | 6200 | 9440 | 14880 | 27200 | 46400 |
| FF/GLY | 52000 | 32400 | 17600 | 11200 | 7320 | 4900 | 3000 | 2116 | 2888 | 4620 | 6840 | 10400 | 16160 | 30000 | 49600 |

The results for different parameters (EVA flat) are shown in Table 9.

TABLE 9

|  | TEX PG CONTROL | TEX GLY | TREV PG | TREV GLY | OP PG | OP GLY | FF PG | FF GLY |
|---|---|---|---|---|---|---|---|---|
| 60 Deg Gloss | 0.9 | 1.4 | 1.7 | 1.8 | 1.9 | 1.9 | 1.9 | 1.9 |
| L* | 96 | 96 | 96 | 96 | 96.1 | 96.1 | 96.1 | 96.1 |
| a* | −0.7 | −0.8 | −0.7 | −0.7 | −0.7 | −0.7 | −0.7 | −0.7 |
| b* | 1.8 | 1.8 | 1.9 | 1.9 | 1.9 | 1.9 | 1.9 | 1.9 |
| Opacity (Y) | 92.2 | 92.8 | 92.2 | 92.5 | 92.5 | 92.8 | 92.5 | 92.9 |
| VOC CALCULATED | 27.6 | 14.0 | 14.0 | 0.0 | 27.6 | 14.0 | 27.6 | 14.0 |

Figure 3:
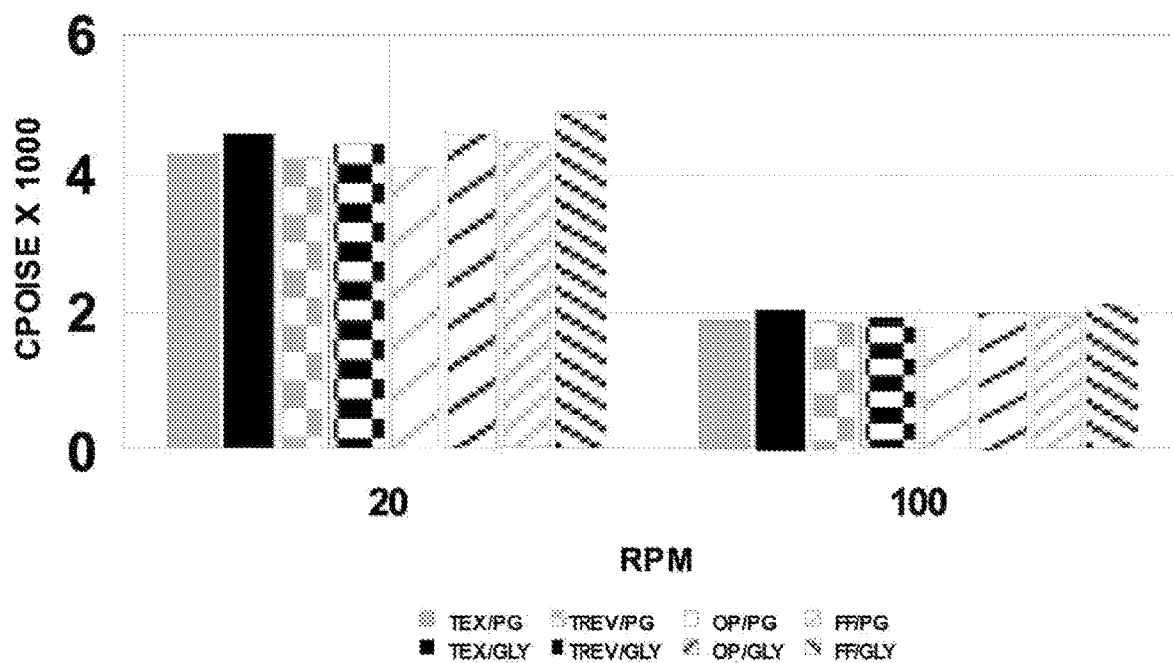
FIG. 3 is a bar graph showing the viscosity at 20 rpm and 100 rpm in an EVA Flat formula.

FIG. 3 shows the viscosity results in graphical form.

Example 7

EVA Semi Gloss Formula

Bis(2-ButoxyEthyl Carbonate) was tested in a number of water-based flat paints, as set out in Example 3. Table 10 shows materials and combinations tested in an EVA semi gloss formula.

TABLE 10

| FORMULATION EVA SEMI-GLOSS | | | | | | | | |
|---|---|---|---|---|---|---|---|---|
|  | A | B | C | D | E | F | G | H |
| WATER | | | | 316.0 | | | | |
| COLLOIDS 226 | | | | 3.0 | | | | |
| IGEPAL CO-630 | | | | 2.0 | | | | |
| AMP-95 | | | | 4.5 | | | | |
| COLLIDS 691 | | | | 6.0 | | | | |
| TIO2(R-706) | | | | 150.0 | | | | |
| HUBERCARB 3G | | | | 80.0 | | | | |
| NATROSOL PLUS | | | | 2.0 | | | | |
| ECOVAE 405 | | | | 408.0 | | | | |
| ACRYSOL TT-935 | | | | 8.0 | | | | |
| AMMONIA | | | | 8.0 | | | | |
| TEXANOL | 5.0 | 5.0 | | | | | | |
| TREVISOL | | | 5.0 | 5.0 | | | | |
| OPTIFILM 400 | | | | | 5.0 | 5.0 | | |
| UCAR FILM IBT | | | | | | | 5.0 | 5.0 |
| PROPYLENE GLYCOL | 5.0 | | 5.0 | | 5.0 | | 5.0 | |
| GLYKOSOL | | 5.0 | | 5.0 | | 5.0 | | 5.0 |

The results for the viscosities (EVA semi gloss) are shown in Table 11.

TABLE 11

| CQ217022 EVA SEMIGLOSS | | | | | | | | | | | | | | | | |
|---|---|---|---|---|---|---|---|---|---|---|---|---|---|---|---|---|
|  | 0.5 | 1 | 2.5 | 5 | 10 | 20 | 50 | 100 | 50 | 20 | 10 | 5 | 2.5 | 1 | 0.5 |
| TEX/PG | 21200 | 13600 | 7440 | 4760 | 3140 | 3110 | 1304 | 954 | 1284 | 2000 | 2900 | 4360 | 6720 | 12400 | 20400 |
| TEX/GLY | 22400 | 14400 | 7920 | 5160 | 3420 | 2340 | 1460 | 1038 | 1404 | 2180 | 3160 | 4720 | 7200 | 13600 | 22400 |
| TREV/PG | 20000 | 12800 | 7040 | 4560 | 3020 | 2040 | 1268 | 912 | 1224 | 1910 | 2780 | 4200 | 6480 | 12000 | 19200 |
| TREV/GLY | 22800 | 14200 | 7920 | 5080 | 3380 | 2280 | 1420 | 1018 | 1380 | 2150 | 3100 | 4640 | 7120 | 13200 | 21600 |
| OP/PG | 20400 | 13000 | 7120 | 4640 | 3060 | 2070 | 1284 | 920 | 1244 | 1940 | 2820 | 4240 | 6640 | 12200 | 20400 |
| OP/GLY | 22800 | 14400 | 8080 | 5200 | 3460 | 2330 | 1448 | 1040 | 1408 | 2190 | 3080 | 4760 | 7280 | 13600 | 21600 |
| FF/PG | 20800 | 13000 | 7200 | 4680 | 3100 | 2060 | 1292 | 938 | 1268 | 1980 | 2880 | 4360 | 6800 | 12600 | 20400 |
| FF/GLY | 21200 | 13800 | 7680 | 5040 | 3380 | 2310 | 1448 | 1046 | 1416 | 2200 | 3180 | 4760 | 7280 | 13400 | 21600 |

The results for different parameters (EVA semi gloss) are shown in Table 12.

TABLE 12

|  | TEX PG CONTROL | TEX GLY | TREV PG | TREV GLY | OP PG | OP GLY | FF PG | FF GLY |
|---|---|---|---|---|---|---|---|---|
| 60 Deg Gloss | 29.9 | 29.9 | 29.8 | 30.2 | 30.3 | 30.6 | 30.7 | 30.3 |
| L* | 96.6 | 96.5 | 96.5 | 96.4 | 96.6 | 96.6 | 96.6 | 96.5 |
| a* | −0.8 | −0.8 | −0.8 | −0.7 | −0.8 | −0.7 | −0.8 | −0.8 |
| b* | 0.9 | 1.0 | 0.9 | 1.0 | 1.0 | 1.0 | 0.9 | 1.0 |
| Opacity (Y) | 93.4 | 93.3 | 9.9 | 93.1 | 92.9 | 92.7 | 93.0 | 92.6 |
| DRY TIME MINUTES | 40 | 35 | 32 | 35 | 35 | 35 | 35 | 40 |
| VOC CALCULATED | 34.7 | 17.6 | 17.7 | 0.0 | 34.7 | 17.7 | 34.7 | 17.7 |

Example 8

Styrene Acrylic Flat Formula

Bis(2-ButoxyEthyl Carbonate) was tested in a number of water-based flat paints, as set out in Example 3. Table 13 shows materials and combinations tested in a styrene acrylic flat formula.

TABLE 13

| FORMULATION STRYENE ACRYLIC FLAT | | | | | | | | |
|---|---|---|---|---|---|---|---|---|
| | A | B | C | D | E | F | G | H |
| WATER | | | | 233.9 | | | | |
| COLLOIDS 226 | | | | 3.0 | | | | |
| IGEPAL CO-630 | | | | 2.0 | | | | |
| AMP-95 | | | | 4.8 | | | | |
| COLLIDS 691 | | | | 6.0 | | | | |
| NATROSOL PLUS | | | | 6.0 | | | | |
| TIO2(R-706) | | | | 150.0 | | | | |
| HUBERCARB 3G | | | | 250.0 | | | | |
| ENCOR 471 | | | | 350.0 | | | | |
| ENCOR 471 | | | | 350.0 | | | | |
| TEXANOL | 30.2 | 30.2 | — | — | — | — | — | — |
| TREVISOL | — | — | 30.2 | 30.2 | — | — | — | — |
| OPTIFILM 400 | — | — | — | — | 30.2 | 30.2 | — | — |
| UCAR FILM IBT | — | — | — | — | — | — | 30.2 | 30.2 |
| PROPYLENE GLYCOL | 23.0 | — | 23.0 | — | 23.0 | — | 23.0 | — |
| GLYOKSOL | — | 23.0 | — | 23.0 | — | 23.0 | — | 23.0 |

The results for different parameters (styrene acrylic flat) are shown in Table 14.

TABLE 14

| | TEX PG CONTROL | TEX GLY | TREV PG | TREV GLY | OP PG | OP GLY | FF PG | FF GLY |
|---|---|---|---|---|---|---|---|---|
| 60 Deg Gloss | 2.1 | 2.1 | 2.2 | 2.2 | 2.2 | 2.2 | 2.2 | 2.1 |
| L* | 96.2 | 96.3 | 96.1 | 96.4 | 96.2 | 96.3 | 96.2 | 96.2 |
| a* | -0.9 | -0.9 | -0.9 | -0.9 | -0.9 | -0.9 | -0.9 | -0.9 |
| b* | 1.6 | 1.6 | 1.5 | 1.5 | 1.5 | 1.5 | 1.5 | 1.5 |
| Opacity (Y) | 93.1 | 93.4 | 92.8 | 93.4 | 92.8 | 93.4 | 93.4 | 92.8 |
| VOC CALCULATED | 129.6 | 77.5 | 60.8 | 0.0 | 130.1 | 78.2 | 129.9 | 78.2 |
| DRY TIME MINUTES | 35 | 35 | 40 | 30 | 35 | 45 | 28 | 25 |

Figure 4:
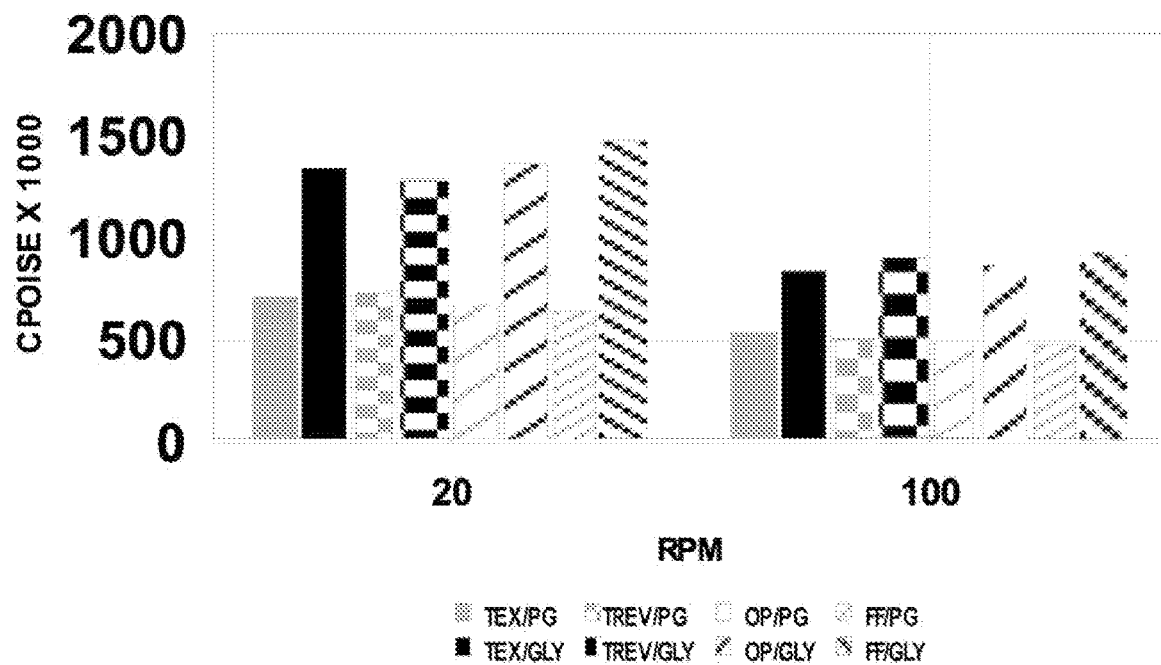
FIG. 4 is a bar graph showing the viscosity at 20 rpm and 100 rpm in a Styrene Acrylic Flat formula.

FIG. 4 shows the viscosity results (styrene acrylic flat) in graphical form.

Example 9

Styrene Acrylic Semi Gloss Formula

Bis(2-ButoxyEthyl Carbonate) was tested in a number of water-based flat paints, as set out in Example 3. Table 15 shows materials and combinations tested in a styrene acrylic semi gloss formula.

TABLE 15

| FORMULATION STRYENE ACRYLIC SEMI-GLOSS | | | | | | | | |
|---|---|---|---|---|---|---|---|---|
| | A | B | C | D | E | F | G | H |
| WATER | | | | 402.4 | | | | |
| COLLOIDS 224 | | | | 10.7 | | | | |
| IGEPAL CO-630 | | | | 4.0 | | | | |
| AMP-95 | | | | 5.3 | | | | |
| COLLIDS 691 | | | | 8.0 | | | | |
| NATROSOL PLUS | | | | 4.0 | | | | |
| TIO2(R-706) | | | | 150.6 | | | | |

TABLE 15-continued

FORMULATION STRYENE ACRYLIC SEMI-GLOSS

|  | A | B | C | D | E | F | G | H |
|---|---|---|---|---|---|---|---|---|
| HUBERCARB 3G |  |  |  | 34.2 |  |  |  |  |
| ENCOR 471 |  |  |  | 381.1 |  |  |  |  |
| ACRYSOL TT-935 |  |  |  | 3.3 |  |  |  |  |
| AMMONIA |  |  |  | 2.7 |  |  |  |  |
| ENCOR 471 |  |  |  | 381.1 |  |  |  |  |
| TEXANOL | 30.2 | 30.2 | — | — | — | — | — | — |
| TREVISOL | — | — | 30.2 | 30.2 | — | — | — | — |
| OPTIFILM 400 | — | — | — | — | 30.2 | 30.2 | — | — |
| UCAR FILM IBT | — | — | — | — | — | — | 30.2 | 30.2 |
| PROPYLENE GLYCOL | 23.0 | — | 23.0 | — | 23.0 | — | 23.0 | — |
| GLYOKSOL | — | 23.0 | — | 23.0 | — | 23.0 | — | 23.0 |

The results for different parameters (styrene acrylic semi gloss) are shown in Table 16.

TABLE 16

|  | TEX PG CONTROL | TEX GLY | TREV PG | TREV GLY | OP PG | OP GLY | FF PG | FF GLY |
|---|---|---|---|---|---|---|---|---|
| 60 Deg Gloss | 6.8 | 13.7 | 6.3 | 14.9 | 5.2 | 12.5 | 6.0 | 14.0 |
| L* | 96.0 | 95.6 | 96.3 | 96.4 | 96.4 | 96.5 | 96.4 | 95.9 |
| a* | −0.8 | −0.8 | −0.8 | −0.8 | −0.8 | −0.8 | −0.8 | −0.8 |
| b* | 0.7 | 0.7 | 0.7 | 0.7 | 0.7 | 0.7 | 0.7 | 0.7 |
| Opacity (Y) | 90.2 | 90.9 | 90.1 | 90.4 | 90.8 | 90.1 | 90.5 | 90.7 |
| VOC CALCULATED | 197.2 | 121.3 | 97.0 | 0.0 | 198.3 | 122.8 | 197.8 | 122.5 |
| DRY TIME MINUTES | 55 | 50 | 45 | 30 | 50 | 25 | 25 | 45 |

Figure 5:
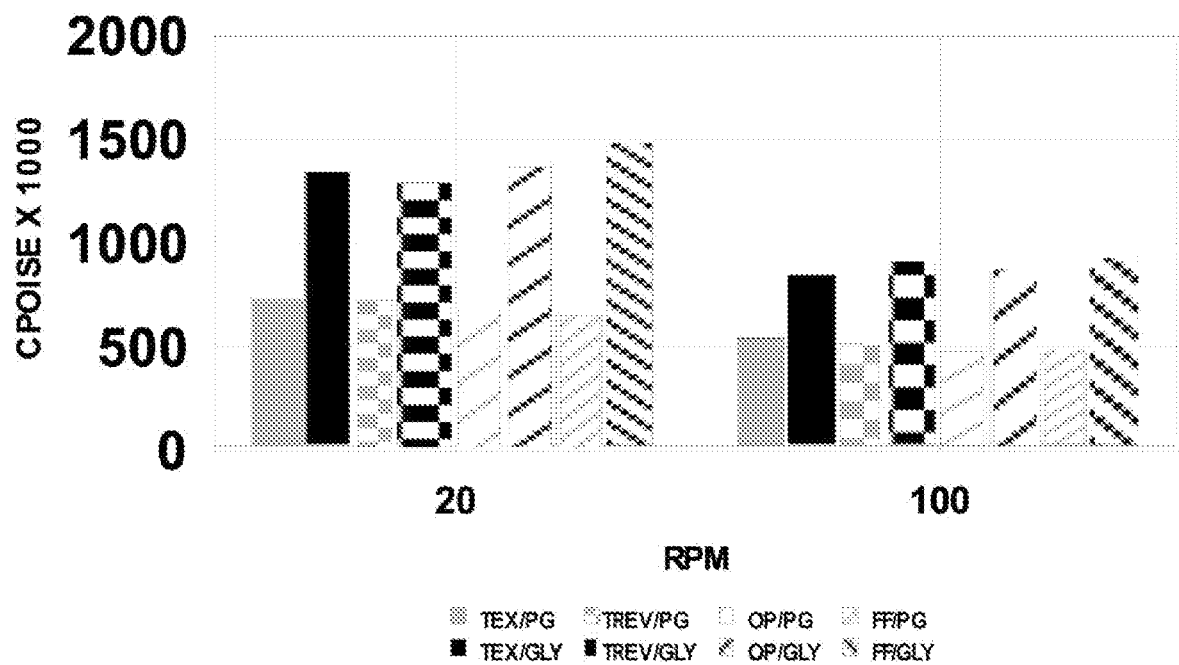
FIG. 5 is a bar graph showing the viscosity at 20 rpm and 100 rpm in a Styrene Acrylic Semi Gloss formula.

FIG. 5 shows the viscosity results (styrene acrylic semi gloss) in graphical form.

Example 10

Acrylic Semi Gloss Formula

Bis(2-ButoxyEthyl Carbonate) was tested in a number of water-based flat paints, as set out in Example 3. Table 17 shows materials and combinations tested in an acrylic semi gloss formula.

TABLE 17

FORMULATION ACRYLIC SEMI-GLOSS

|  | A | B | C | D | E | F | G | H |
|---|---|---|---|---|---|---|---|---|
| WATER |  |  |  | 223.0 |  |  |  |  |
| AMP-95 |  |  |  | 3.2 |  |  |  |  |
| COLLOIDS 226 |  |  |  | 8.0 |  |  |  |  |
| COLLIDS 691 |  |  |  | 4.0 |  |  |  |  |
| TIO2(R-706) |  |  |  | 152.0 |  |  |  |  |
| HUBERCARB 3G |  |  |  | 78.0 |  |  |  |  |
| ENCOR 662 |  |  |  | 530.0 |  |  |  |  |
| ACRYSOL TT-935 |  |  |  | 10.0 |  |  |  |  |
| AMMONIA |  |  |  | 10.0 |  |  |  |  |
| TEXANOL | 8.3 | 8.3 |  |  |  |  |  |  |
| TREVISOL |  |  | 8.3 | 8.3 |  |  |  |  |
| OPTIFILM 400 |  |  |  |  | 8.3 | 8.3 |  |  |
| UCAR FILM IBT |  |  |  |  |  |  | 8.3 | 8.3 |
| PROPYLENE GLYCOL | 20.0 |  | 20.0 |  | 20.0 |  | 20.0 |  |
| GLYKOSOL |  | 20.0 |  | 20.0 |  | 20.0 |  | 20.0 |

The results for the viscosities (acrylic semi gloss) are shown in Table 18.

TABLE 18

| CQ217018 ACRYLIC SEMIGLOSS | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 12400 | 7200 | 3840 | 2400 | 1520 | 990 | 600 | 422 | 600 | 1000 | 1520 | 2400 | 3760 | 6800 | 11600 |
| TEX/GLY | 8800 | 6400 | 4160 | 2920 | 2200 | 1720 | 1280 | 1018 | 1272 | 1680 | 2100 | 2760 | 3760 | 5800 | 7600 |
| TREV/PG | 11600 | 6600 | 3520 | 2240 | 1480 | 1000 | 644 | 482 | 640 | 980 | 1420 | 2120 | 3280 | 6000 | 10000 |
| TREV/GLY | 6000 | 5200 | 5760 | 3640 | 3080 | 2670 | 2156 | 1700 | 2156 | 2660 | 3060 | 3560 | 4240 | 6200 | 6800 |
| OP/PG | 9600 | 6600 | 3520 | 2240 | 1480 | 1000 | 636 | 476 | 636 | 980 | 1420 | 2160 | 3360 | 6200 | 10000 |
| OP/GLY | 5600 | 5000 | 3920 | 3200 | 2620 | 2220 | 1764 | 1418 | 1764 | 2190 | 2580 | 3080 | 3840 | 4800 | 5600 |
| FF/PG | 11200 | 7000 | 3760 | 2320 | 1500 | 980 | 596 | 426 | 596 | 970 | 1460 | 2280 | 3680 | 7000 | 11600 |
| FF/GLY | 7200 | 6400 | 4160 | 3000 | 2260 | 1770 | 1324 | 1056 | 1316 | 1730 | 2180 | 2880 | 3840 | 6000 | 8400 |

The results for different parameters (acrylic semi gloss) are shown in Table 19.

TABLE 19

| | TEX PG CONTROL | TEX GLY | TREV PG | TREV GLY | OP PG | OP GLY | FF PG | FF GLY |
|---|---|---|---|---|---|---|---|---|
| 20 Deg Gloss | 6.9 | 6.7 | 6.8 | 6.8 | 7.1 | 7.2 | 7.2 | 6.9 |
| 60 Deg Gloss | 30.4 | 29.4 | 29.7 | 29.7 | 30.5 | 30.4 | 30.9 | 30.5 |
| L* | 96.1 | 96.6 | 96.6 | 96.8 | 96.6 | 96.7 | 96.7 | 96.7 |
| a* | −0.8 | −0.8 | −0.8 | −0.8 | −0.8 | −0.7 | −0.8 | −0.8 |
| b* | 0.8 | 0.8 | 0.8 | 1 | 0.9 | 0.9 | 0.9 | 0.9 |
| Opacity (Y) | 93.7 | 94.3 | 93.7 | 94.1 | 94.1 | 94.3 | 93.8 | 94.2 |
| VOC (CALCULATED) | 133.6 | 43.1 | 98.8 | 0.0 | 134.1 | 43.3 | 134.0 | 43.2 |
| DRY TIME MINUTES | 15 | 20 | 25 | 30 | 20 | 30 | 25 | 30 |

Figure 6A:
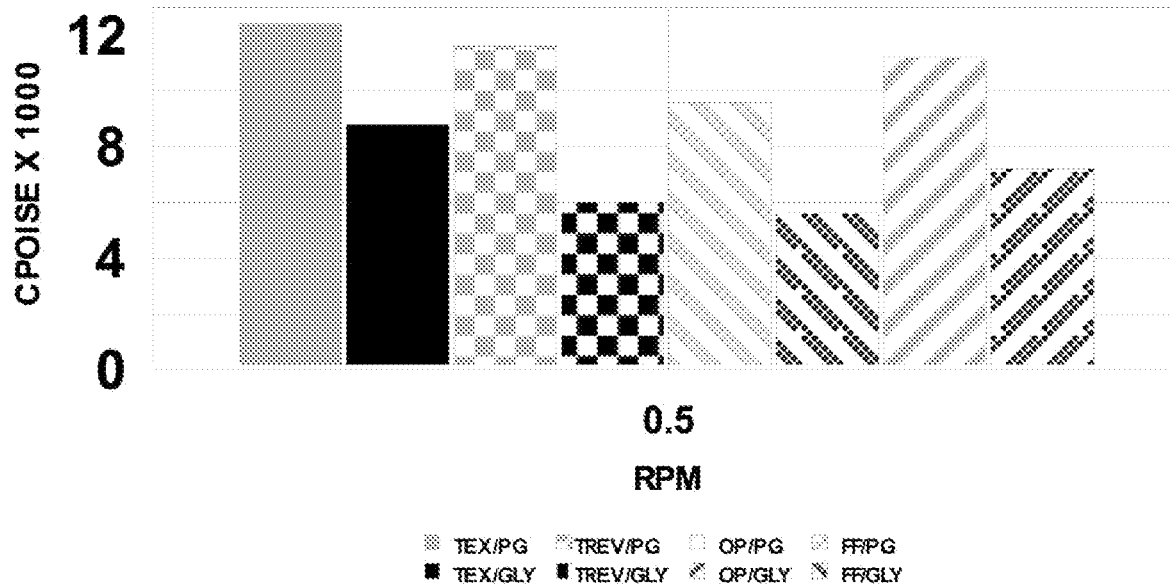
FIG. 6A is a bar graph showing the viscosity at 0.5 rpm, #4 spindle, in an Acrylic Semi Gloss formula.
Figure 6B:
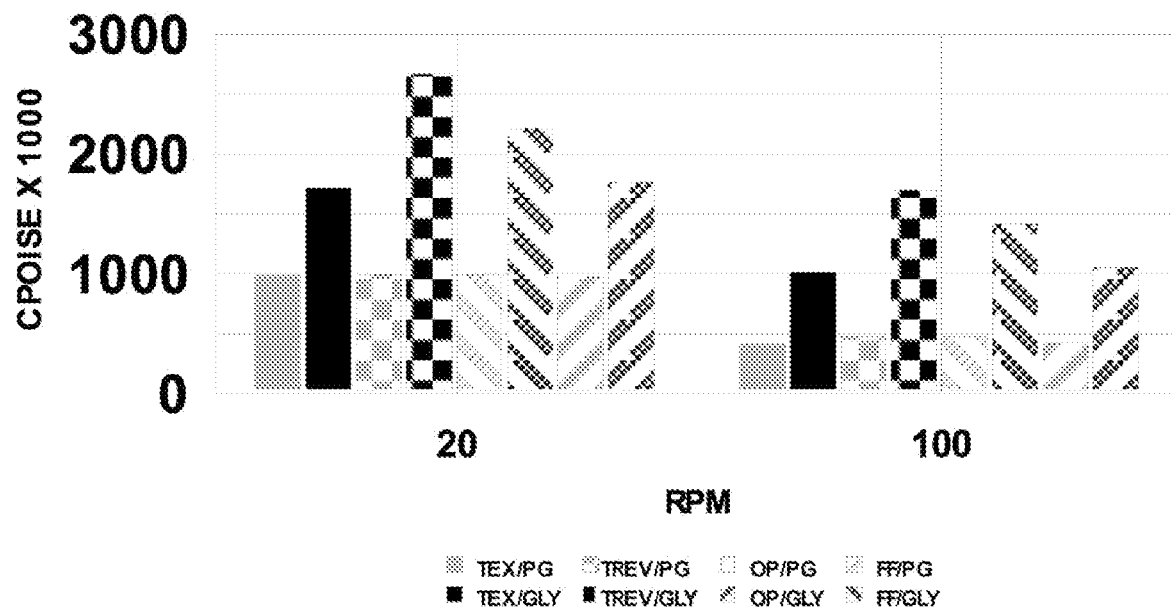
FIG. 6B is a bar graph showing the viscosity at 20 rpm and 100 rpm, #4 spindle, in an Acrylic Semi Gloss formula.
Figure 6C:
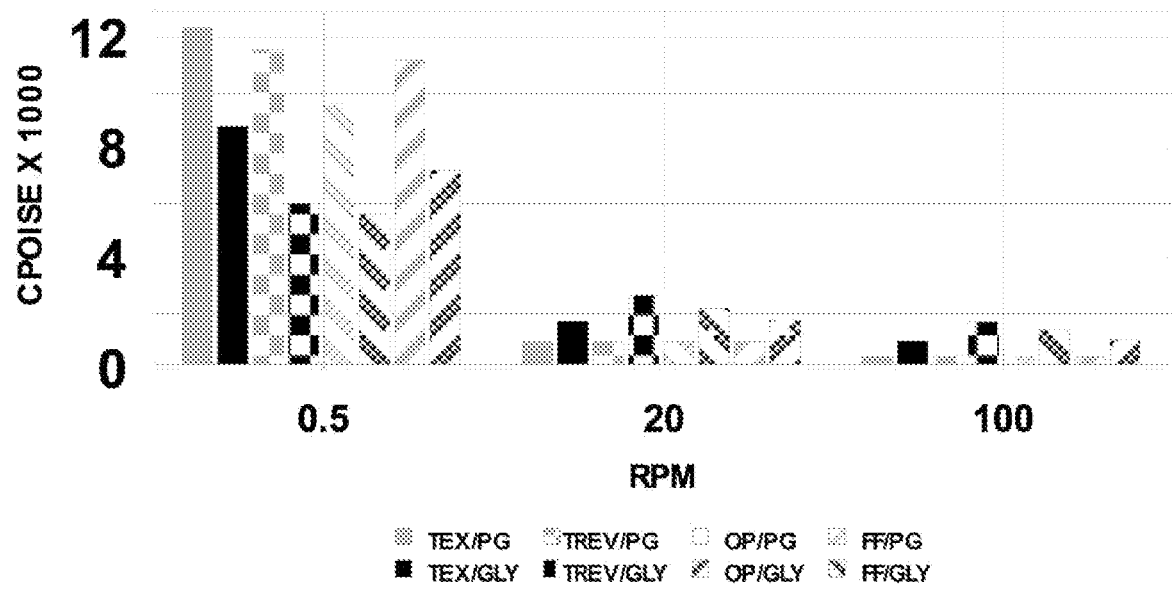
FIG. 6C is a bar graph showing the viscosity at 0.5 rpm, 20 rpm and 100 rpm, #4 spindle, in an Acrylic Semi Gloss formula.

FIGS. 6A-C show the viscosity results (acrylic semi gloss) in graphical form, where TEX is Texanol™, PG is Propylene Glycol, GLY is GlykoSol, OP is Optifilm™ 400, and FF is Film Former IBT.

Example 11

Acrylic Flat Formula

Bis(2-ButoxyEthyl Carbonate) was tested in a number of water-based flat paints, as set out in Example 3.

The results for the viscosities (acrylic flat) are shown in Table 20.

TABLE 20

| CQ218002 ACRYLIC FLAT | | | | | | | | | | | | | | | |
|---|---|---|---|---|---|---|---|---|---|---|---|---|---|---|---|
| | 0.5 | 1 | 2.5 | 5 | 10 | 20 | 50 | 100 | 50 | 20 | 10 | 5 | 2.5 | 1 | 0.5 |
| TEX/PG | 1400 | 1300 | 1240 | 1000 | 840 | 715 | 596 | 542 | 624 | 735 | 820 | 900 | 1000 | 1200 | 1400 |
| TEX/GLY | 3800 | 3800 | 3000 | 2240 | 1720 | 1345 | 1020 | 842 | 1004 | 1240 | 1440 | 1660 | 1920 | 2200 | 2800 |
| TREV/PG | 1600 | 1500 | 1320 | 1040 | 860 | 725 | 586 | 508 | 588 | 700 | 780 | 840 | 960 | 1200 | 1200 |
| TREV/GLY | 2800 | 2800 | 2360 | 1940 | 1580 | 1295 | 1080 | 907 | 1088 | 1355 | 1560 | 1800 | 2040 | 2400 | 2800 |
| OP/PG | 1200 | 1300 | 1200 | 940 | 790 | 665 | 542 | 479 | 548 | 640 | 720 | 780 | 880 | 1000 | 1200 |
| OP/GLY | 4800 | 4100 | 2760 | 2160 | 1720 | 1375 | 1050 | 867 | 1046 | 1320 | 1550 | 1800 | 2080 | 2500 | 2800 |
| FF/PG | 1400 | 1300 | 1080 | 920 | 760 | 650 | 540 | 478 | 544 | 635 | 700 | 760 | 880 | 900 | 1000 |
| FF/GLY | 4400 | 4200 | 3280 | 2500 | 1890 | 1485 | 1122 | 922 | 1108 | 1395 | 1630 | 1900 | 2200 | 2600 | 3000 |

Figure 7A:
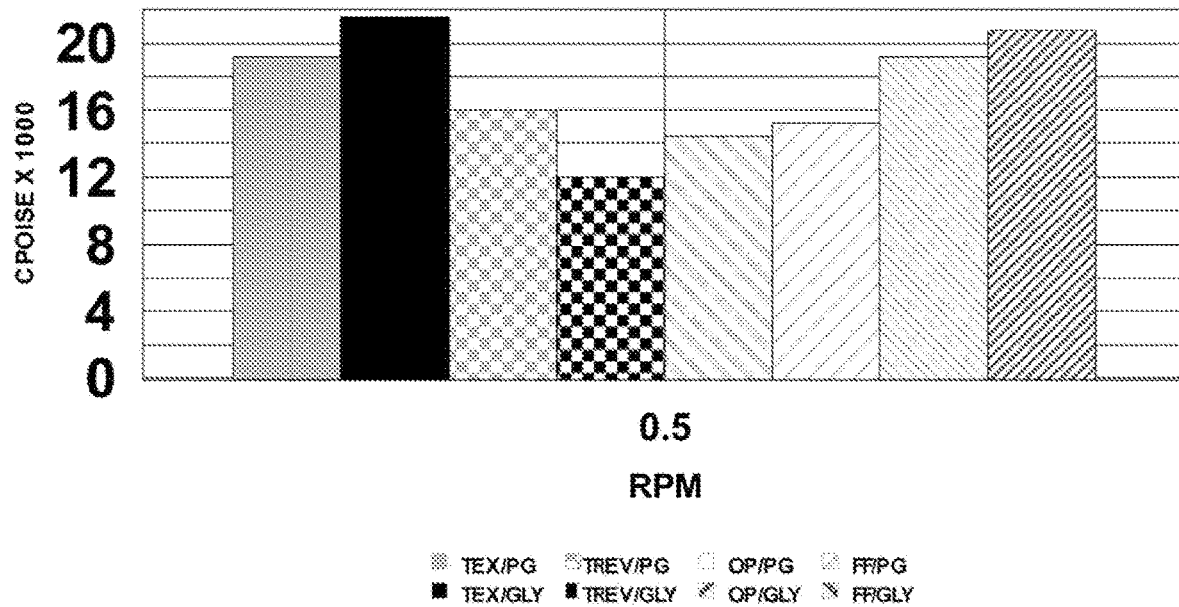
FIG. 7A is a bar graph showing the viscosity at 0.5 rpm, #5 spindle, in an Acrylic Flat formula.
Figure 7B:
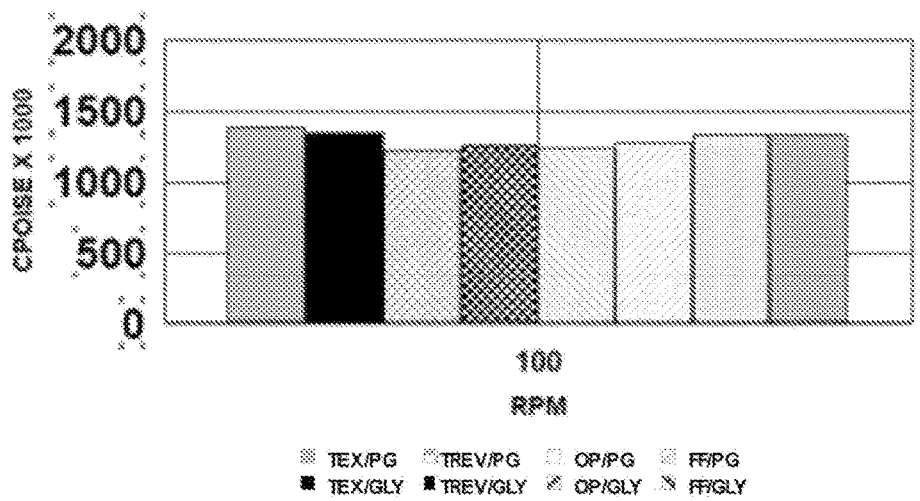
FIG. 7B is a bar graph showing the viscosity at 100 rpm, #5 spindle, in an Acrylic Flat formula.
Figure 7C:
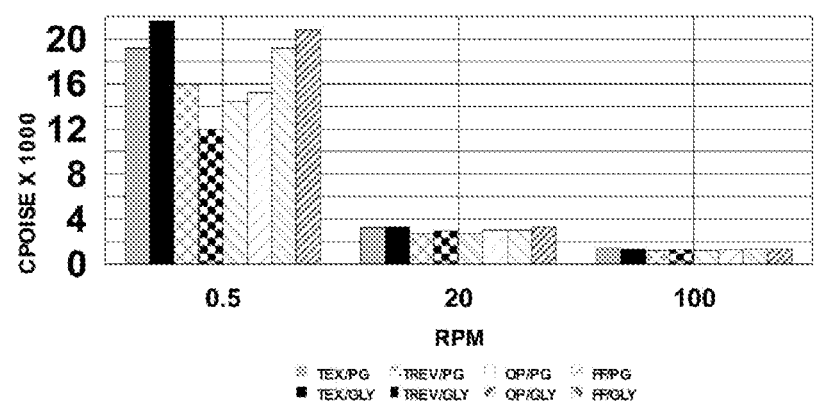
FIG. 7C is a bar graph showing the viscosity at 0.5 rpm, 20 rpm and 100 rpm, #5 spindle, in an Acrylic Flat formula.

FIGS. 7A-C show the viscosity results (acrylic flat) in graphical form.

Example 12

Texanol Comparison

Bis(1-butoxypropan-2-yl) carbonate (TreviSol, XTR5) was also tested to evaluate its performance against Texanol in forming a cohesive film at various temperatures. Scrubs were done after one week dry time using ASTM-D2486; blocking was done after one week dry time using ASTM-D4946-89; and the Minimum Film Forming Temperature (MFFT_ was done by ASTM D 2354 using Rhopoint TE-MFFT-9011.

The MMFT results were as follows (MFFT ENCOR 471):
a. resin only, greater that 33° C.;
b. 3% Texanol, 22.6° C.;
c. 3% TreviSol, 19.9° C.;
d. 4% Texanol; 22.6° C.;
e. 4% TreviSol, 13° C.;
f. 5% Texanol, 13.4° C.;
g. 5% TreviSol, 7.3° C.;
h. 6% Texanol, 10.6° C.;
i. 6% TreviSol, less than −1° C.

The results showed that bis(1-butoxypropan-2-yl) carbonate (TreviSol, XTR5) is far more efficient at forming a film at similar temperatures but that it may also form a film as low as −1 deg C. By contrast, the lowest temperature Texanol could form a film was 10.6 Deg C.

Furthermore, the ASTM D 2486 scrub tests showed that when a film is fully coalesced using bis(1-butoxypropan-2-yl) carbonate (TreviSol, XTR5), it has greater integral strength and far more resistant to burnishing, marking, scuffs and abrasion. Thus, a film using bis(1-butoxypropan-2-yl) carbonate (TreviSol, XTR5) as the coalescent solvent in the formula is far more efficient than Texanol and less bis(1-butoxypropan-2-yl) carbonate (TreviSol, XTR5) can be used.

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined by the claims appended hereto.

What is claimed is:

1. A compound of Formula (I):

Formula (I)

R—O—CH₂—CH(CH₃)—O—C(=O)—O—CH(CH₃)—CH₂—O—R wherein R is $C_{1-12}$ alkyl, optionally substituted from one up to the maximum number of substituents with oxygen.

2. The compound of claim 1, wherein the compound is:

[structure]

3. The compound of claim 1, wherein the compound is:

[structure]

4. The compound of claim 1, wherein the compound is a coalescent.

5. The compound of claim 4 wherein the compound is an inert coalescent or a film forming coalescent.

6. The compound of claim 1, wherein the compound is a retarding solvent.

7. The compound of claim 1, wherein the compound is a substitute for an ester alcohol.

8. The compound of claim 1, wherein the compound is a reactive intermediate in the formation of an ester derivative for a plasticizer.

9. The compound of claim 1, wherein the compound is a component in a thickener.

10. The compound of claim 1, wherein the compound is an inert ingredient in an insecticide, fungicide or rodenticide formulation.

11. A kit or commercial package comprising the compound of claim 1, together with instructions for use.

12. A method of forming a coating on a substrate, the method comprising applying a compound of Formula (I):

Formula (I)

R—O—CH₂—CH(CH₃)—O—C(=O)—O—CH(CH₃)—CH₂—O—R wherein R is $C_{1-12}$ alkyl, optionally substituted from one up to the maximum number of substituents with oxygen, to the substrate.

13. The method of claim 12, wherein the compound is:

[structure]

14. The method of claim 12, wherein the compound is:

[structure]

15. The method of claim 12, wherein the compound is provided in admixture with a paint.

16. The compound of claim 2, wherein the compound is a coalescent.

17. The compound of claim 3, wherein the compound is a coalescent.

18. A kit or commercial package comprising the compound of claim 2 together with instructions for use.

19. A kit or commercial package comprising the compound of claim 3 together with instructions for use.

* * * * *